(12) United States Patent
Baker et al.

(10) Patent No.: US 8,337,523 B2
(45) Date of Patent: Dec. 25, 2012

(54) TISSUE FIXATION ASSEMBLY HAVING PREPOSITIONED FASTENERS AND METHOD

(75) Inventors: Steve G. Baker, Redmond, WA (US); Brett J. Carter, Monroe, WA (US); Stefan J. M. Kraemer, Seattle, WA (US); Clifton A. Alferness, Port Orchard, WA (US); John M. Adams, Sammamish, WA (US); Raymond Michael Wolniewicz, III, Redmond, WA (US)

(73) Assignee: EndoGastric Solutions, Inc., Redmond, WA (US)

( * ) Notice: Subject to any disclaimer, the term of this patent is extended or adjusted under 35 U.S.C. 154(b) by 565 days.

(21) Appl. No.: 12/460,247

(22) Filed: Jul. 15, 2009

(65) Prior Publication Data
US 2010/0023028 A1   Jan. 28, 2010

Related U.S. Application Data

(63) Continuation of application No. 11/172,363, filed on Jun. 29, 2005, now abandoned, which is a continuation-in-part of application No. 10/783,717, filed on Feb. 20, 2004, now abandoned.

(51) Int. Cl.
*A61B 17/10*   (2006.01)
*A61B 17/08*   (2006.01)

(52) U.S. Cl. ......... 606/215; 606/139; 606/151; 606/213
(58) Field of Classification Search .................. 606/151, 606/213, 139, 157, 215; 600/585
See application file for complete search history.

(56) References Cited

U.S. PATENT DOCUMENTS

| | | | | |
|---|---|---|---|---|
| 4,921,479 | A | * | 5/1990 | Grayzel .......................... 604/509 |
| 2005/0043759 | A1 | * | 2/2005 | Chanduszko .................. 606/213 |

* cited by examiner

*Primary Examiner* — Corrine M McDermott
*Assistant Examiner* — Melissa Ryckman
(74) *Attorney, Agent, or Firm* — Jens E. Hoekendijk

(57) ABSTRACT

A tissue fastener assembly delivers a fastener for deployment. The assembly includes a fastener including a first member, a second member, the first and second members having first and second ends, and a flexible connecting member fixed to each of the first and second members intermediate the first and second ends and extending between the first and second members. The first member has a longitudinal axis and a through channel along the axis. The assembly further includes a deployment wire slidingly received within the through channel of the first member that pierces into the tissue and guides the first member through the tissue, a guide structure defining a lumen that receives the fastener and deployment wire and guides the deployment wire and fastener to the tissue, and a fastener configuration structure that orientates the second member in a predetermined position relative to the first member within the lumen for dependable deployment.

4 Claims, 20 Drawing Sheets

TISSUE FIXATION ASSEMBLY HAVING PREPOSITIONED FASTENERS AND METHOD

RELATED APPLICATION DATA

The present application is a continuation application of U.S. application Ser. No. 11/172,363, filed on Jun. 29, 2005, now abandoned, which is a continuation-in-part of U.S. application Ser. No. 10/783,717, filed on Feb. 20, 2004, now abandoned. The full disclosures of which are hereby incorporated for all purposes.

FIELD OF THE INVENTION

The present invention generally relates to tissue fixation devices, and more particularly to assemblies for deploying the same. The present invention more particularly relates to such assemblies wherein tissue fixation fasteners are prepositioned for reliable deployment.

BACKGROUND

Gastroesophageal reflux disease (GERD) is a chronic condition caused by the failure of the anti-reflux barrier located at the gastroesophageal junction to keep the contents of the stomach from splashing into the esophagus. The splashing is known as gastroesophageal reflux. The stomach acid is designed to digest meat, and will digest esophageal tissue when persistently splashed into the esophagus.

A principal reason for regurgitation associated with GERD is the mechanical failure of a deteriorated gastroesophageal flap to close and seal against high pressure in the stomach. Due to reasons including lifestyle, a Grade I normal gastroesophageal flap may deteriorate into a malfunctioning Grade III or absent valve Grade IV gastroesophageal flap. With a deteriorated gastroesophageal flap, the stomach contents are more likely to be regurgitated into the esophagus, the mouth, and even the lungs. The regurgitation is referred to as "heartburn" because the most common symptom is a burning discomfort in the chest under the breastbone. Burning discomfort in the chest and regurgitation (burping up) of sour-tasting gastric juice into the mouth are classic symptoms of gastroesophageal reflux disease (GERD). When stomach acid is regurgitated into the esophagus, it is usually cleared quickly by esophageal contractions. Heartburn (backwashing of stomach acid and bile onto the esophagus) results when stomach acid is frequently regurgitated into the esophagus and the esophageal wall is inflamed.

Complications develop for some people who have GERD. Esophagitis (inflammation of the esophagus) with erosions and ulcerations (breaks in the lining of the esophagus) can occur from repeated and prolonged acid exposure. If these breaks are deep, bleeding or scarring of the esophagus with formation of a stricture (narrowing of the esophagus) can occur. If the esophagus narrows significantly, then food sticks in the esophagus and the symptom is known as dysphagia. GERD has been shown to be one of the most important risk factors for the development of esophageal adenocarcinoma. In a subset of people who have severe GERD, if acid exposure continues, the injured squamous lining is replaced by a precancerous lining (called Barrett's Esophagus) in which a cancerous esophageal adenocarcinoma can develop.

Other complications of GERD may not appear to be related to esophageal disease at all. Some people with GERD may develop recurrent pneumonia (lung infection), asthma (wheezing), or a chronic cough from acid backing up into the esophagus and all the way up through the upper esophageal sphincter into the lungs. In many instances, this occurs at night, while the person is in a supine position and sleeping. Occasionally, a person with severe GERD will be awakened from sleep with a choking sensation. Hoarseness can also occur due to acid reaching the vocal cords, causing a chronic inflammation or injury.

GERD never improves without intervention. Life style changes combined with both medical and surgical treatments exist for GERD. Medical therapies include antacids and proton pump inhibitors. However, the medical therapies only mask the reflux. Patients still get reflux and perhaps emphysema because of particles refluxed into the lungs. Barrett's esophagus results in about 10% of the GERD cases. The esophageal epithelium changes into tissue that tends to become cancerous from repeated acid washing despite the medication.

Several open laparotomy and laproscopic surgical procedures are available for treating GERD. One surgical approach is the Nissen fundoplication. The Nissen approach typically involves a 360-degree wrap of the fundus around the gastroesophageal junction. The procedure has a high incidence of postoperative complications. The Nissen approach creates a 360-degree moveable flap without a fixed portion. Hence, Nissen does not restore the normal movable flap. The patient cannot burp because the fundus was used to make the repair, and may frequently experience dysphagia. Another surgical approach to treating GERD is the Belsey Mark IV (Belsey) fundoplication. The Belsey procedure involves creating a valve by suturing a portion of the stomach to an anterior surface of the esophagus. It reduces some of the postoperative complications encountered with the Nissen fundoplication, but still does not restore the normal movable flap. None of these procedures fully restores the normal anatomical anatomy or produces a normally functioning gastroesophageal junction. Another surgical approach is the Hill repair. In the Hill repair, the gastroesophageal junction is anchored to the posterior abdominal areas, and a 180-degree valve is created by a system of sutures. The Hill procedure restores the moveable flap, the cardiac notch and the Angle of His. However, all of these surgical procedures are very invasive, regardless of whether done as a laproscopic or an open procedure.

New, less surgically invasive approaches to treating GERD involve transoral endoscopic procedures. One procedure contemplates a machine device with robotic arms that is inserted transorally into the stomach. While observing through an endoscope, an endoscopist guides the machine within the stomach to engage a portion of the fundus with a corkscrew-like device on one arm. The arm then pulls on the engaged portion to create a fold of tissue or radial plication at the gastroesophageal junction. Another arm of the machine pinches the excess tissue together and fastens the excess tissue with one pre-tied implant. This procedure does not restore normal anatomy. The fold created does not have anything in common with a valve. In fact, the direction of the radial fold prevents the fold or plication from acting as a flap of a valve.

Another transoral procedure contemplates making a fold of fundus tissue near the deteriorated gastroesophageal flap to recreate the lower esophageal sphincter (LES). The procedure requires placing multiple U-shaped tissue clips around the folded Fundus to hold it in shape and in place.

This and the previously discussed procedure are both highly dependent on the skill, experience, aggressiveness, and courage of the endoscopist. In addition, these and other procedures may involve esophageal tissue in the repair. Esophageal tissue is fragile and weak. Involvement of esophageal tissue in the repair of a gastroesophageal flap valve poses unnecessary risks to the patient.

A new and improved apparatus and method for restoration of a gastroesophageal flap valve is fully disclosed in U.S. Pat. No. 6,790,214, is assigned to the assignee of this invention, and is incorporated herein by reference. That apparatus and method provides a transoral endoscopic gastroesophageal flap valve restoration. A longitudinal member arranged for transoral placement into a stomach carries a tissue shaper that non-invasively grips and shapes stomach tissue. A tissue fixation device is then deployed to maintain the shaped stomach tissue in a shape approximating and restoring a gastroesophageal flap.

Whenever tissue is to be maintained in a shape as, for example, in the improved assembly last mentioned above, it is necessary to fasten at least two layers of tissue together. In applications such as gastroesophageal flap valve restoration, there is very limited room to maneuver a fastener deployment device. For example, this and other medical fastening applications provide confined working channels and spaces and often must be fed through an endoscope to permit visualization or other small lumen guide catheters to the place where the fasteners are to be deployed. To make matters worse, multiple fasteners may also be required. Hence, with current fasteners and deployment arrangements, it is often difficult to direct a single fastener to its intended location, let alone a number of such fasteners.

Once the fastening site is located, the fasteners employed must be truly able to securely maintain the tissue. Also, quite obviously, the fasteners are preferably deployable in the tissue in a manner which does not unduly traumatize the tissue. Moreover, the fasteners and deployment assemblies must assure dependable operation to negate the need for repeated deployment attempts.

SUMMARY

The invention provides a fastener assembly comprising a fastener including a first member, a second member, the first and second members having first and second ends, and a flexible connecting member fixed to each of the first and second members intermediate the first and second ends and extending between the first and second members. The first member has a longitudinal axis and a through channel along the axis. The assembly further comprises a deployment wire slidingly received within the through channel of the first member that pierces into the tissue and guides the first member through the tissue, a guide structure defining a lumen that receives the fastener and deployment wire and guides the deployment wire and fastener to the tissue, and a fastener configuration structure that orientates the second member in a predetermined position relative to the first member within the lumen.

The fastener configuration structure orientates the second member along side the first member. The fastener configuration structure orientates the second member along side the first member with the connecting member between the first and second members. The fastener configuration structure orientates the second member along side the first member with the connecting member between the first and second members and with the second member trailing the first member with respect to the tissue.

The first member of the fastener may have a lengthwise slit communicating with the through channel and the deployment wire may be received into the through channel through the slit.

The assembly may further comprise a fastener loader that guides the first member slit into engagement with the deployment wire. The fastener loader is preferably arranged to hold a plurality of the fasteners. The fastener configuration structure may comprise a wall converging with the deployment wire and an outlet communicating with the lumen. The wall preferably converges with the deployment wire in a direction towards the tissue so that, when the second member engages the wall, the wall directs the second member to the predetermined position relative to the first member. The wall thus orientates the second member along side the first member.

The invention further provides a fastener assembly comprising a fastener including a first member, a second member, the first and second members having first and second ends, and a flexible connecting member fixed to each of the first and second members intermediate the first and second ends and extending between the first and second members. The first member has a longitudinal axis and a through channel along the axis. The assembly further comprises a deployment wire slidingly received within the through channel of the first member that pierces into the tissue and guides the first member through the tissue, and a guide structure defining a lumen that receives the fastener and deployment wire and guides the deployment wire and fastener to the tissue. The second member of the fastener is along side the first member with the connecting member between the first and second members within the lumen.

The invention still further provides a method comprising providing a fastener including a first member, a second member, the first and second members having first and second ends, and a flexible connecting member fixed to each of the first and second members intermediate the first and second ends and extending between the first and second members. The first member has a longitudinal axis and a through channel along the axis. The method further comprises mounting the fastener onto a deployment wire with the deployment wire slidingly received by the through channel of the first member, translating the fastener to within a lumen dimensioned to receive the fastener and deployment wire and which guides the deployment wire and fastener to tissue, and orientating the second member in a predetermined position relative to the first member as the fastener is translated to within the lumen.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like referenced numerals identify like elements, and wherein:

DETAILED DESCRIPTION

Figure 1:
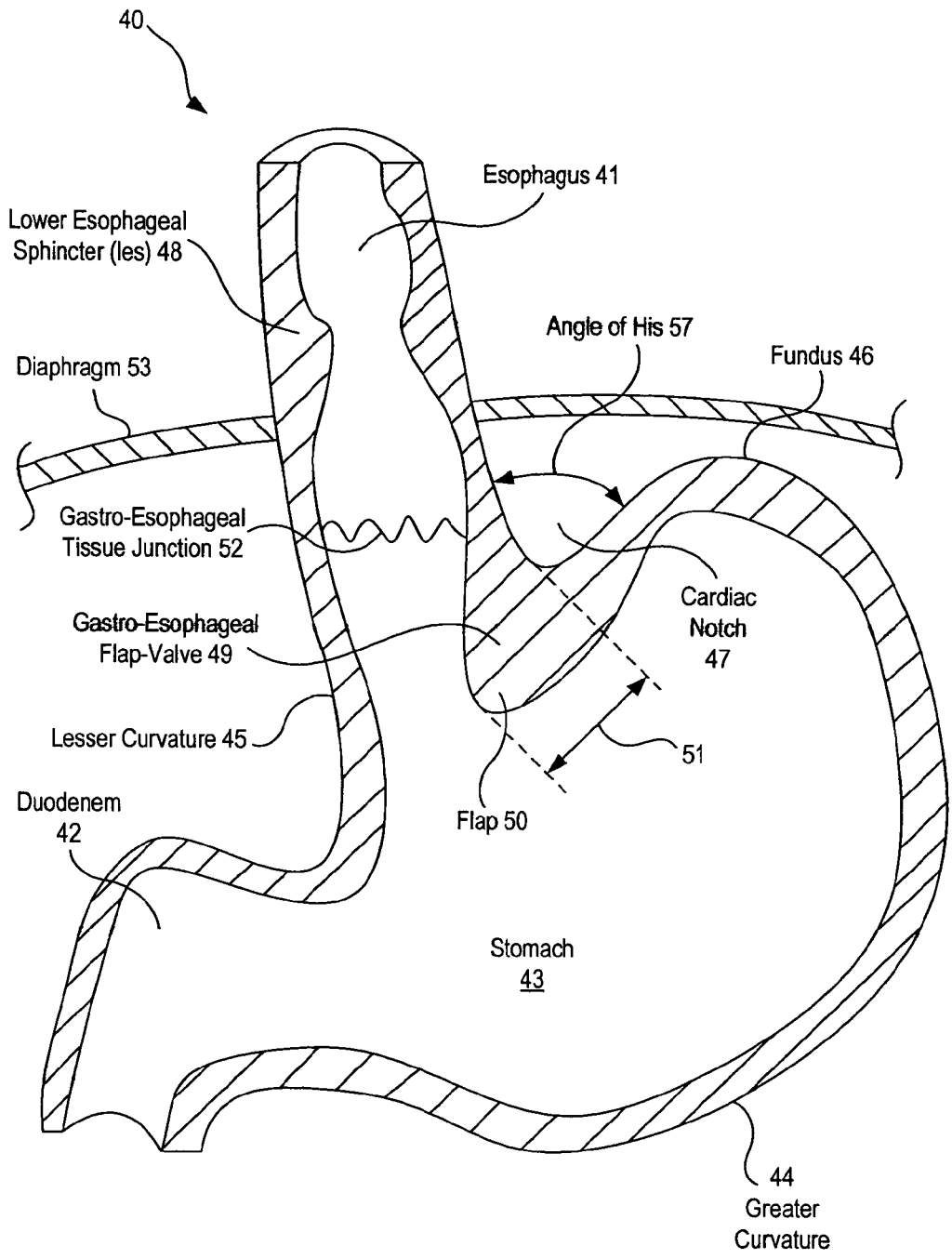
FIG. 1 is a front cross-sectional view of the esophageal-gastro-intestinal tract from a lower portion of the esophagus to the duodenum.

FIG. 1 is a front cross-sectional view of the esophageal-gastro-intestinal tract 40 from a lower portion of the esophagus 41 to the duodenum 42. The stomach 43 is characterized by the greater curvature 44 on the anatomical left side and the lesser curvature 45 on the anatomical right side. The tissue of the outer surfaces of those curvatures is referred to in the art as serosa tissue. As will be seen subsequently, the nature of the serosa tissue is used to advantage for its ability to bond to like serosa tissue. The Fundus 46 of the greater curvature 44 forms the superior portion of the stomach 43, and traps gas and air bubbles for burping. The esophageal tract 41 enters the stomach 43 at an esophageal orifice below the superior portion of the fundus 46, forming a cardiac notch 47 and an acute angle with respect to the Fundus 46 known as the Angle of His 57. The lower esophageal sphincter (LES) 48 is a discriminating sphincter able to distinguish between burping gas, liquids, and solids, and works in conjunction with the Fundus 46 to burp. The gastroesophageal flap valve (GEFV) 49 includes a moveable portion and an opposing more stationary portion. The moveable portion of the GEFV 49 is an approximately 180 degree, semicircular, gastroesophageal flap 50 (alternatively referred to as a "normal moveable flap" or "moveable flap") formed of tissue at the intersection between the esophagus 41 and the stomach 43. The opposing more stationary portion of the GEFV 49 comprises a portion of the lesser curvature 45 of the stomach 43 adjacent to its junction with the esophagus 41. The gastroesophageal flap 50 of the GEFV 49 principally comprises tissue adjacent to the fundus 46 portion of the stomach 43, is about 4 to 5 cm long (51) at it longest portion, and the length may taper at its anterior and posterior ends. The gastroesophageal flap 50 is partially held against the lesser curvature 45 portion of the stomach 43 by the pressure differential between the stomach 43 and the thorax, and partially by the resiliency and the anatomical structure of the GEFV 49, thus providing the valving function. The GEFV 49 is similar to a flutter valve, with the gastroesophageal flap 50 being flexible and closeable against the other more stationary side.

The esophageal tract is controlled by an upper esophageal sphincter (UES) in the neck near the mouth for swallowing, and by the LES 48 and the GEFV 49 at the stomach. The normal anti-reflux barrier is primarily formed by the LES 48 and the GEFV 49 acting in concert to allow food and liquid to enter the stomach, and to considerably resist reflux of stomach contents into the esophagus 41 past the gastroesophageal tissue junction 52. Tissue aboral of the gastroesophageal tissue junction 52 is generally considered part of the stomach because the tissue protected from stomach acid by its own protective mechanisms. Tissue oral of the gastroesophageal junction 52 is generally considered part of the esophagus and it is not protected from injury by prolonged exposure to stomach acid. At the gastroesophageal junction 52, the juncture of the stomach and esophageal tissues form a zigzag line, which is sometimes referred to as the "Z-line." For the purposes of these specifications, including the claims, "stomach" means the tissue aboral of the gastroesophageal junction 52.

Figure 2:
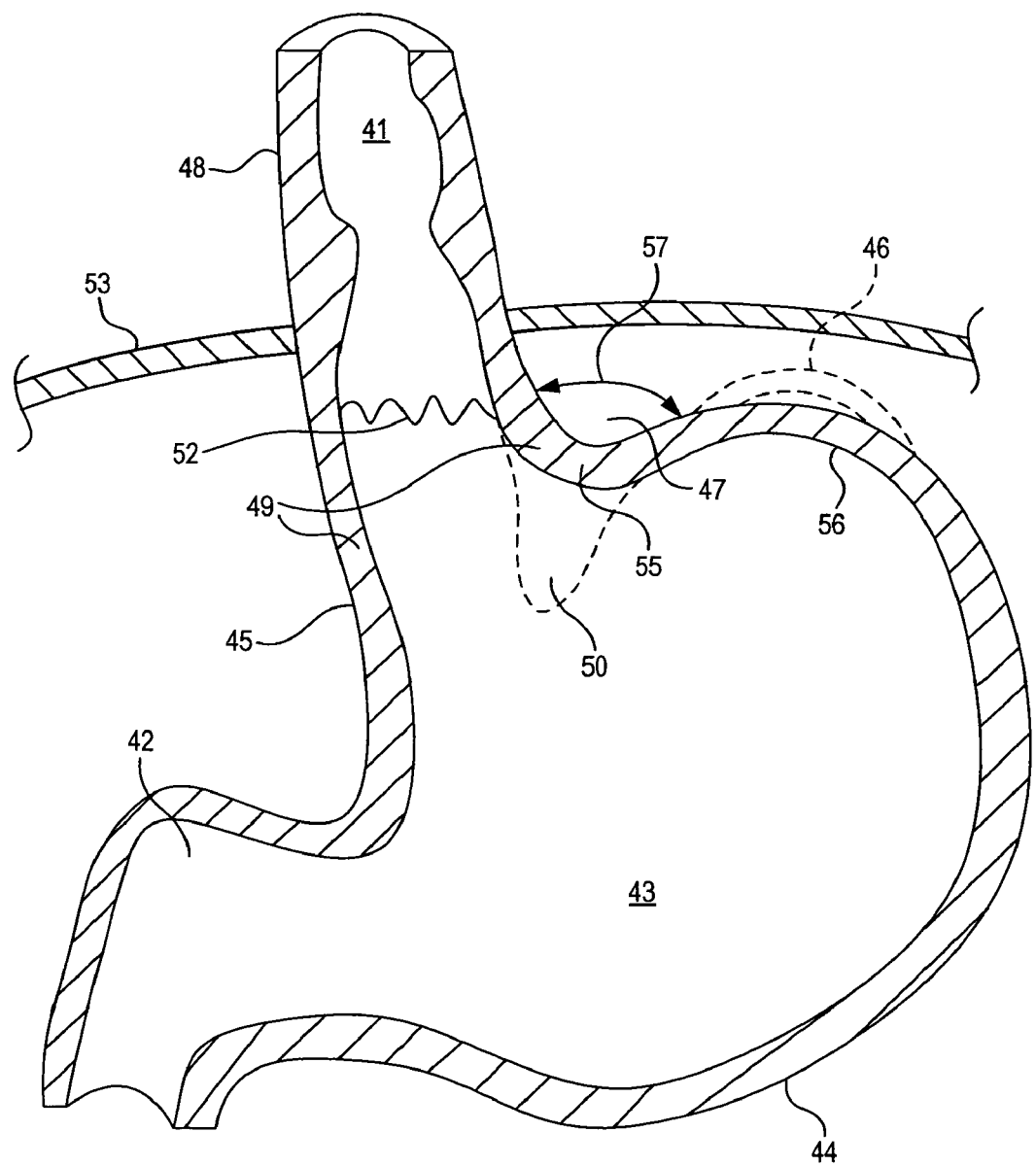
FIG. 2 is a front cross-sectional view of the esophageal-gastro-intestinal tract illustrating a Grade I normal appearance movable flap of the gastroesophageal flap valve (in dashed lines) and a Grade III reflux appearance gastroesophageal flap of the gastroesophageal flap valve (in solid lines)

FIG. 2 is a front cross-sectional view of an esophageal-gastro-intestinal tract illustrating a Grade I normal appearance movable flap 50 of the GEFV 49 (shown in dashed lines) and a deteriorated Grade III gastroesophageal flap 55 of the GEFV 49 (shown in solid lines). As previously mentioned, a principal reason for regurgitation associated with GERD is the mechanical failure of the deteriorated (or reflux appearance) gastroesophageal flap 55 of the GEFV 49 to close and seal against the higher pressure in the stomach. Due to reasons including lifestyle, a Grade I normal gastroesophageal flap 50 of the GEFV 49 may deteriorate into a Grade III deteriorated gastroesophageal flap 55. The anatomical results of the deterioration include moving a portion of the esophagus 41 that includes the gastroesophageal junction 52 and LES 48 toward the mouth, straightening of the cardiac notch 47, and increasing the Angle of His 57. This effectively reshapes the anatomy aboral of the gastroesophageal junction 52 and forms a flattened fundus 56. The deteriorated gastroesophageal flap 55 illustrates a gastroesophageal flap valve 49 and cardiac notch 47 that have both significantly degraded. Dr. Hill and colleagues developed a grading system to describe the appearance of the GEFV and the likelihood that a patient will experience chronic acid reflux. L. D. Hill, et al., *The gastroesophageal flap valve: in vitro and in vivo observations*, Gastrointestinal Endoscopy 1996: 44:541-547. Under Dr. Hill's grading system, the normal movable flap 50 of the GEFV 49 illustrates a Grade I flap valve that is the least likely to experience reflux. The deteriorated gastroesophageal flap 55 of the GEFV 49 illustrates a Grade III (almost Grade IV) flap valve. A Grade IV flap valve is the most likely to experience reflux. Grades II and III reflect intermediate grades of deterioration and, as in the case of III, a high likelihood of experiencing reflux. With the deteriorated GEFV represented by deteriorated gastroesophageal flap 55 and the Fundus 46 moved inferior, the stomach contents are presented a funnel-like opening directing the contents into the esophagus 41 and the greatest likelihood of experiencing reflux. Disclosed subsequently is a device for restoring the normal gastroesophageal flap valve anatomy, which device is one embodiment of the present invention.

Figure 3:
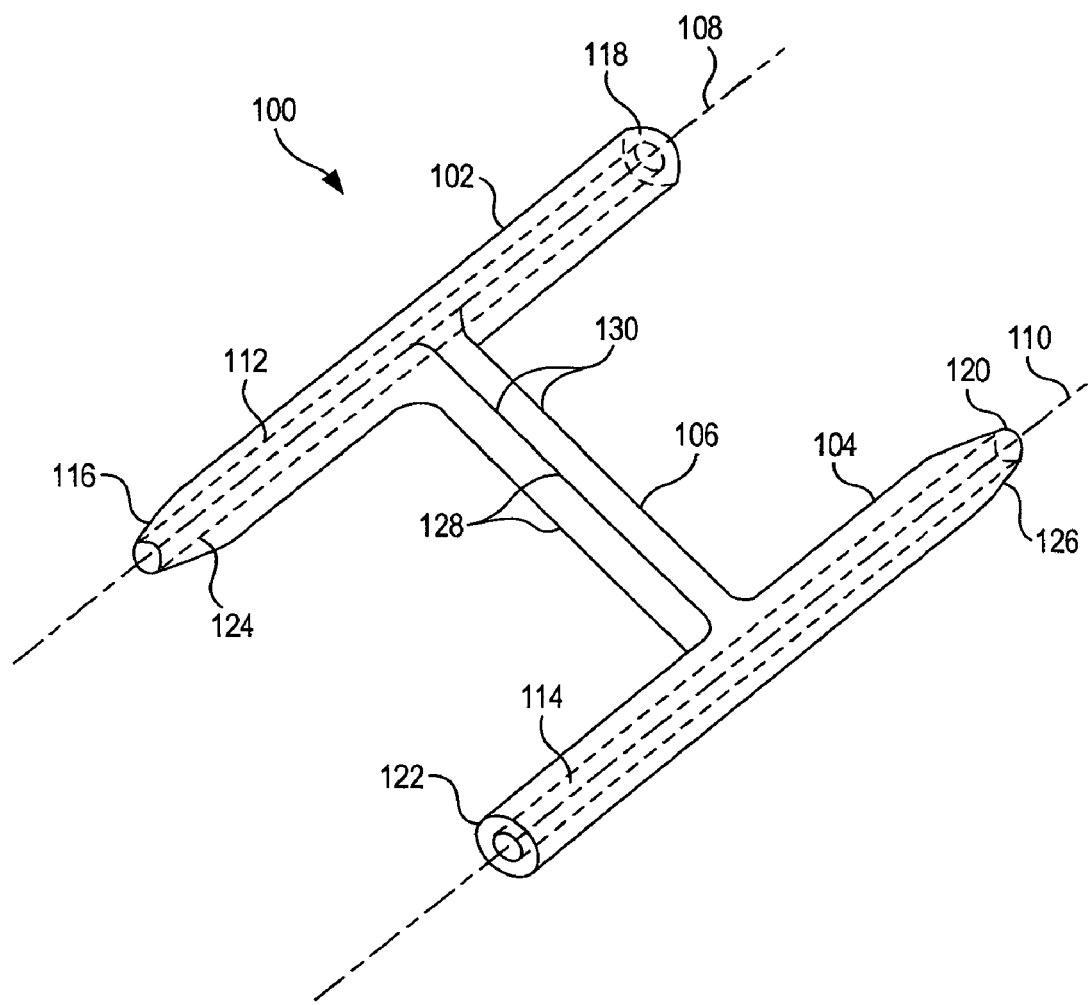
FIG. 3 is a perspective view of a fastener according to an embodiment of the invention.

Referring now to FIG. 3, it is a perspective view of a fastener 100 according to an embodiment of the invention. The fastener 100 generally includes a first member 102, a second member 104, and a connecting member 106. As may be noted in FIG. 3, the first member 102 and second member 104 are substantially parallel and substantially perpendicular to the connecting member 106 which connects the first member 102 to the second member 104.

The first and second members 102 and 104 are generally cylindrical. Each has a longitudinal axis 108 and 110 and a through channel 112 and 114 along the longitudinal axes 108 and 110. The through channels 112 and 114 are formed by through bores which are dimensioned to be slidingly received on a tissue piercing deployment wire to be described hereinafter.

The first member 102 also includes a first end 116 and a second end 118. Similarly, the second member 114 includes a first end 120 and a second end 122. The first ends 116 and 120 form pointed dilation tips 124 and 126, respectively. The dilation tips 124 and 126 are conical and more particularly take the shape of truncated cones. The pointed tips 129 and 126 are pointed in opposite directions.

The first and second members 102 and 104 and the connecting 106 may be formed of different materials and have different textures. These materials may include, for example, plastic materials such as polypropylene, polyethylene, polyglycolic acid, polyurethane, or a thermoplastic elastomer. As may be further noted in FIG. 3, the connecting member 106 has a vertical dimension 128 and a horizontal dimension 130 which is transverse to the vertical dimension. The horizontal dimension is substantially less than the vertical dimension to render the connecting member 106 readily bendable in a horizontal plane. The connecting member is further rendered bendable by the nature of the plastic material from which the fastener 100 is formed. The connecting member may be formed from either an elastic plastic or a permanently deformable plastic. An elastic material would prevent compression necrosis in some applications.

Figure 4:
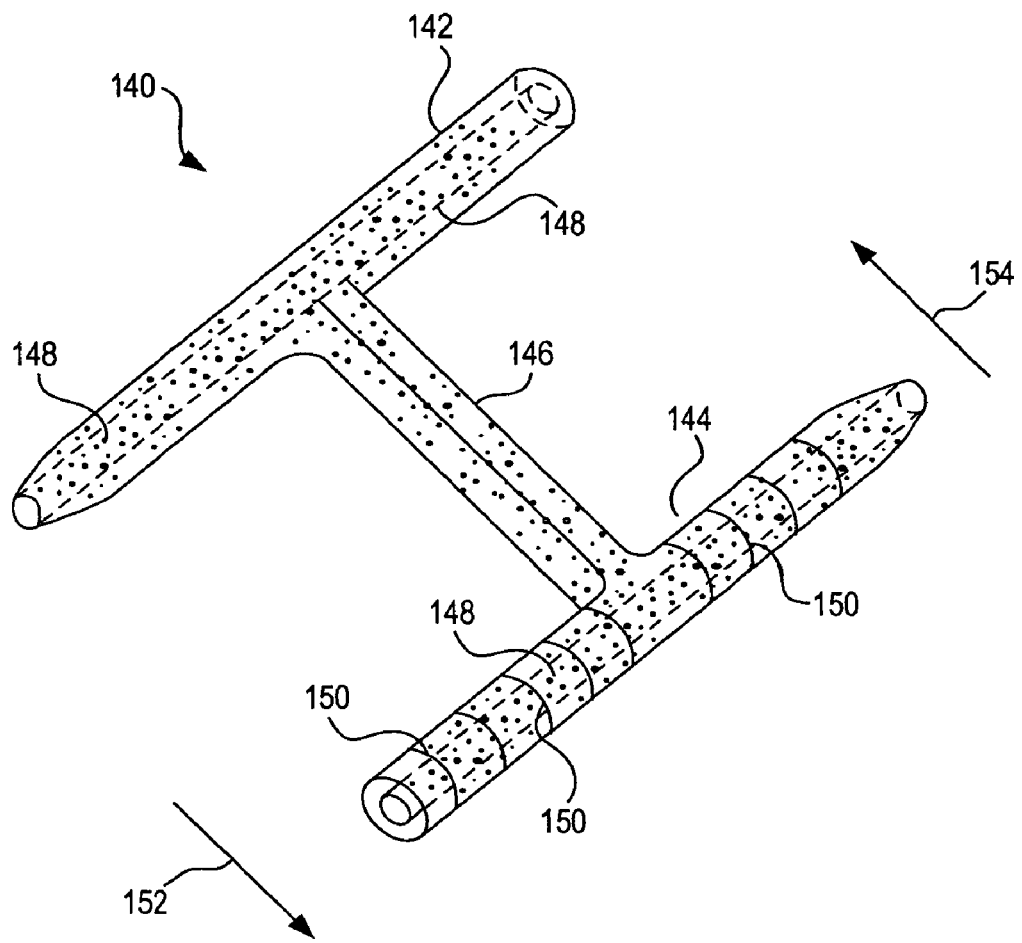
FIG. 4 is a perspective view of another fastener according to an embodiment of the invention.

Referring now to FIG. 4, it illustrates another fastener 140 embodying the present invention. As with the fastener 100 of FIG. 3, the fastener 140 includes a first member 142, a second member 144, and a connecting member 146. The fastener 140 may be formed in one piece and a plastic material similar to the fastener 100 of FIG. 3. The fasteners 100 and 140 may be formed of a plastic material which includes a color pigment, for example pthalocyanine blue, for contrasting with the color of body tissue to enable visualization of the fastener with an endoscope during the deployment of the fasteners. In addition, as may be seen in FIG. 4, the fastener 140 is impregnated with radio opaque material 148 so as to render the fastener 140 at least partially viewable under fluoroscopy. The radio opaque particles may be, for example, barium sulfate, bismuth subcarbonate, tungsten powder or tantalum powder.

In addition to the foregoing, the second member 144 of the fastener 140 includes a plurality of longitudinally spaced vertical slots 150. This renders the second member 144 flexible in a direction opposite the slots but stiff in a direction of the slots. Hence, the second member 144 is resistant to bending in a first direction indicated by arrow 152 while being substantially less resistant to bending in a direction indicated by arrow 154. The reduced resistance to bending in the direction 154 of the second member 144 of the fastener 140 may be utilized to advantage in the deployment of the fastener 140.

Figure 5:
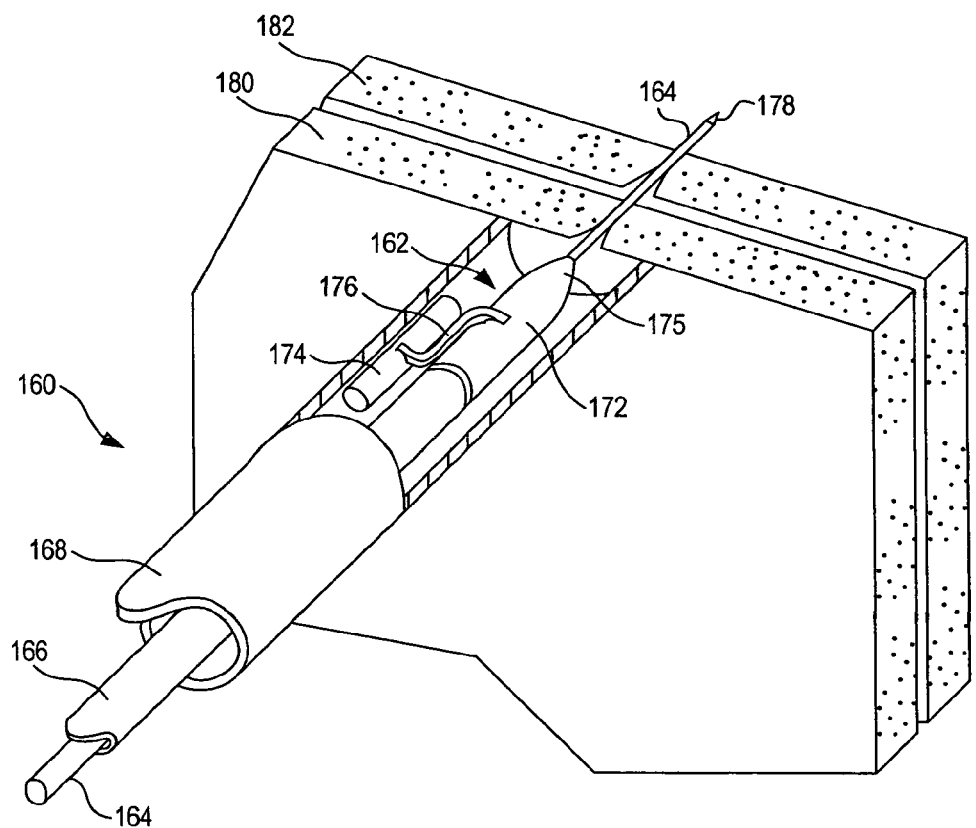
FIG. 5 is a perspective view with portions cut away of a fastener assembly according to an embodiment of the invention with the fastener prepositioned according to this embodiment and in an early stage of deployment.

Referring now to FIG. 5, it is a perspective view with portions cut away of a fastener assembly embodying the present invention. The tissue layer portions above the fastener 162 have been shown cut away in FIGS. 5-9 to enable the deployment procedure to be seen more clearly. The assembly 160 generally includes a fastener 162, a deployment wire 164, a pusher 166, and a guide tube 168.

The fastener 162 takes the form of a further fastener embodiment of the present invention and includes a first member 172, a second member 174, and a connecting member 176. The fastener 162 differs from the fasteners 100 and 140 of FIGS. 3 and 4, respectively, in that the second member 174 is of solid construction and does not include a longitudinal through channel or a pointed tip. However, the first member 172 includes a through channel as previously described and a pointed tip 175.

The first member 172 of the fastener 162 is slidingly received on the deployment wire 164. The deployment wire 164 has a pointed tip 178 for piercing the tissue layers 180 and 182 to be fastened together. As will be seen hereinafter, and in accordance with further aspects of the present invention, the tissue layers 180 and 182 may be folded stomach tissue which are to be fastened and maintained together to form and maintain a gastroesophageal flap valve.

As will be noted in FIG. 5, the tissue piercing wire 164, fastener 162, and the pusher 166 are all within the guide tube 168. The guide tube 168 may take the form of a lumen within most any lumen providing structure such as a catheter, for example.

As will be further noted in FIG. 5, and according to this embodiment of the present invention, the second member 174 is disposed along side the first member 172. This is rendered possible by the flexibility of the connecting member 176. Preferably, the first member, connecting member, and second member are arranged so that the connecting member 176 lies between the first member 172 and the second member 174 and, as illustrated, with the second member 174 trailing the first member 172 with respect to the tissue layers 180 and 182.

With the first member 172 of the fastener 162 slidingly received on the tissue piercing wire 164 and with the pusher 166 just touching the first member 172 on the tissue piercing wire 164, the tip 178 of the tissue piercing wire 164 pierces the tissue layers 180 and 182. The subassembly of the tissue piercing wire 164, fastener 162, and pusher 166 may be guided to its intended location relative to the tissue layers 180 and 182 by the guide tube 168.

Figure 6:
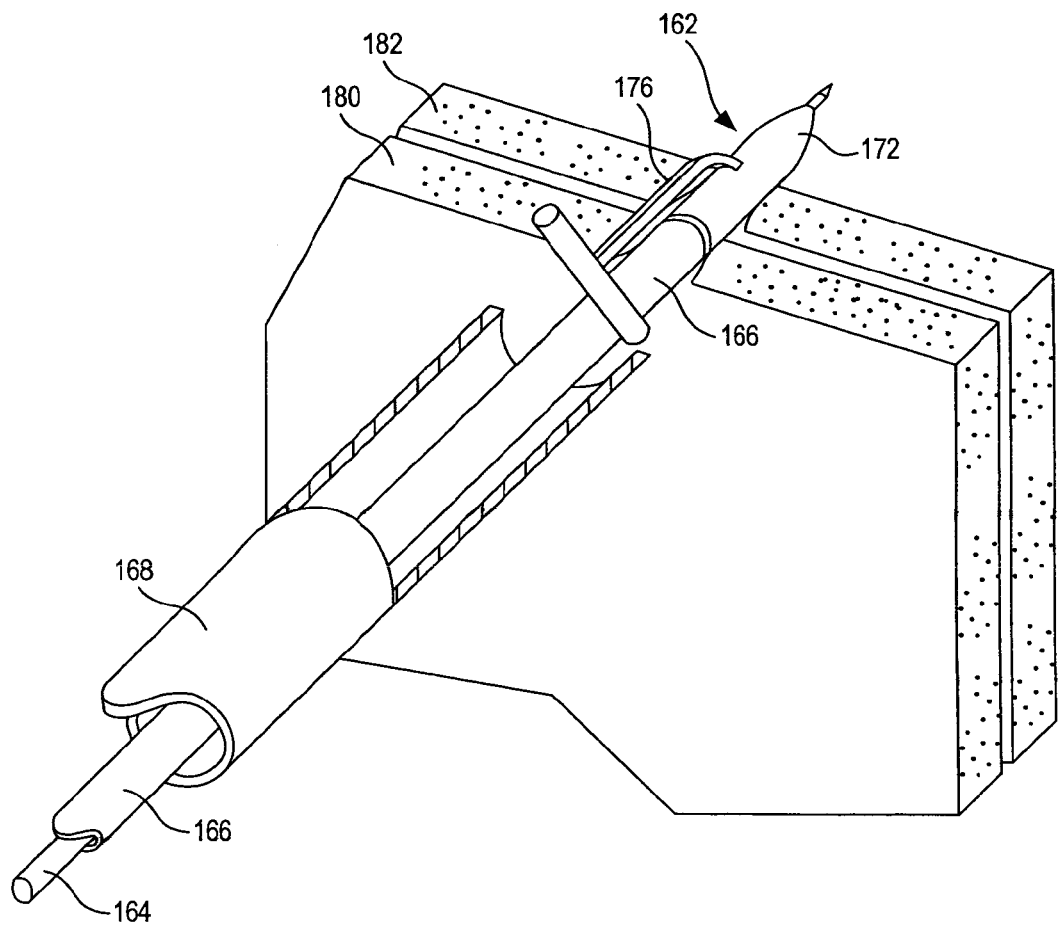
FIG. 6 is a perspective view of the assembly of FIG. 5 shown with the fastener being driven in the tissue layers to be fastened.
Figure 7:
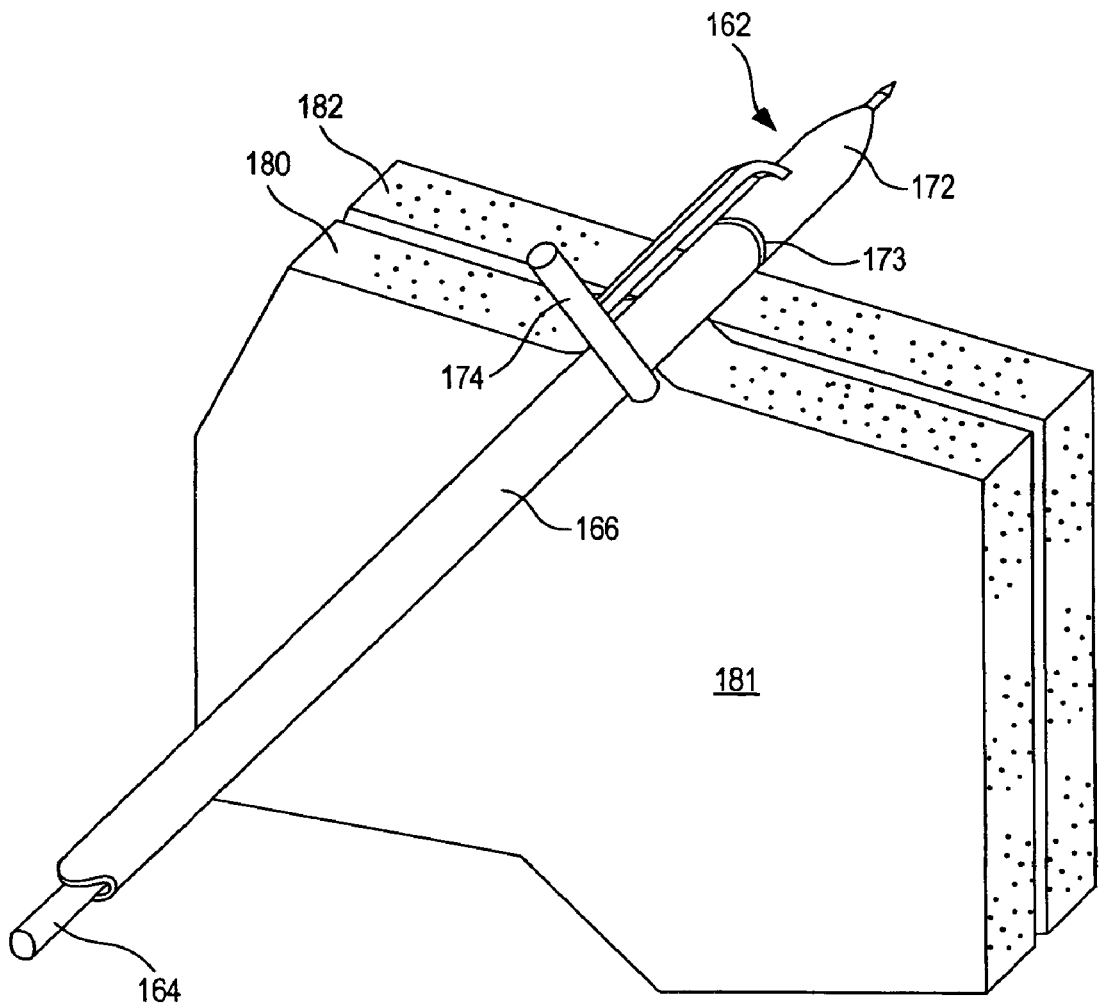
FIG. 7 is a perspective view of the assembly of FIG. 5 shown with the fastener extending through the tissue layers to be fastened.

Once the tissue piercing wire 164 has pierced the tissue layers 180 and 182 to be fastened together, the pusher 166 may be utilized to push the first member 172 of the fastener 162 through the tissue layers 180 and 182 on the tissue piercing wire 164. This is illustrated in FIG. 6. As the pusher 166 pushes the first member 172 through the tissue layers 180 and 182, the connecting member 176 follows along beside and immediately adjacent to the first member 172 of the fastener 162 and the pusher 166. As may be seen in FIG. 7, the pusher 166 continues to push the first member 172 of the fastener 162 through the tissue layers 180 and 182 on the tissue piercing wire 164 until the end 173 of the first member 172 engaging the pusher 166 clears the second tissue layer 182. It may also be noted that at this time, the second member 174 of the fastener 162 has engaged the surface 181 of tissue layer 180.

Figure 8:
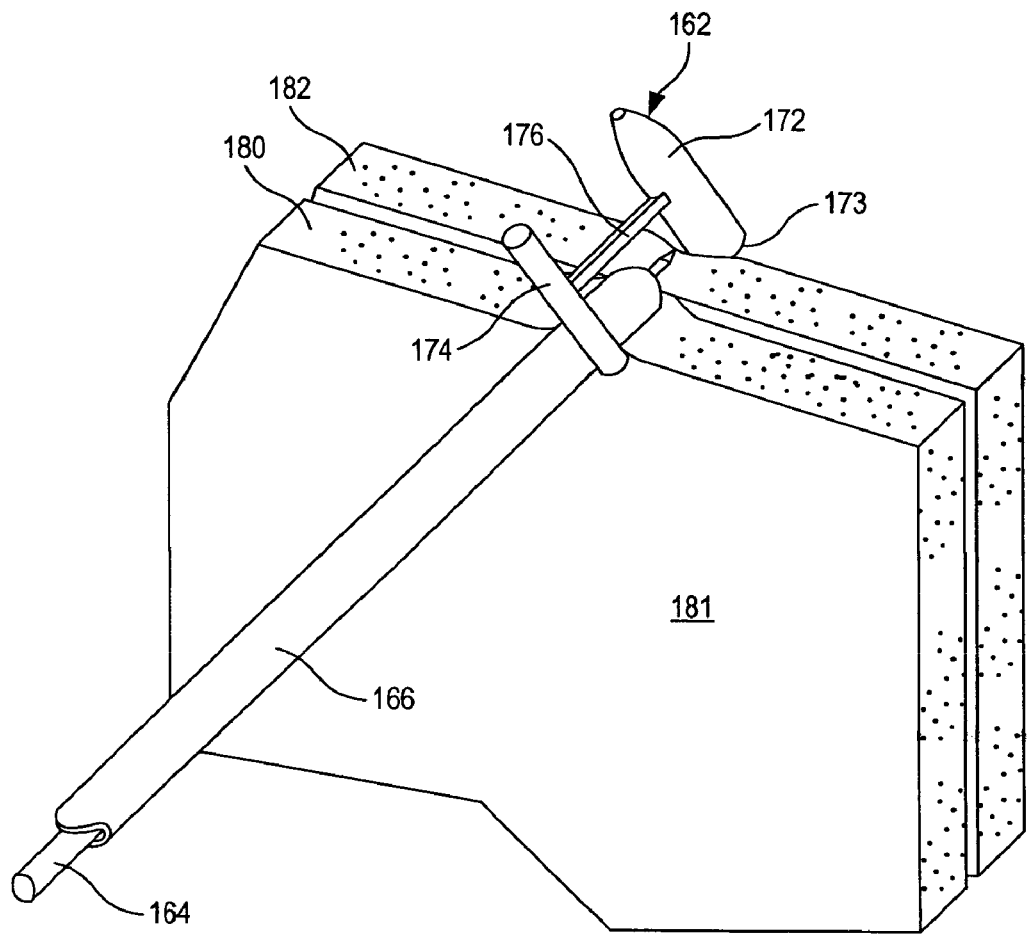
FIG. 8 is a perspective view of the assembly of FIG. 5 shown with the fastener initially deployed.

Referring now to FIG. 8, it will be seen that once the end 173 of the first member 172 has cleared the tissue layer 182, the tissue piercing wire 164 is then retracted within the pusher 166 to release the first member 172. The first member 172 being thus released from the tissue piercing wire 164 will return to its original configuration substantially parallel to the second member 174 and substantially perpendicular to the connecting member 176. When the first member 172 is deployed as shown in FIG. 8, the tissue piercing wire 164 and pusher 166 may be withdrawn.

Figure 9:
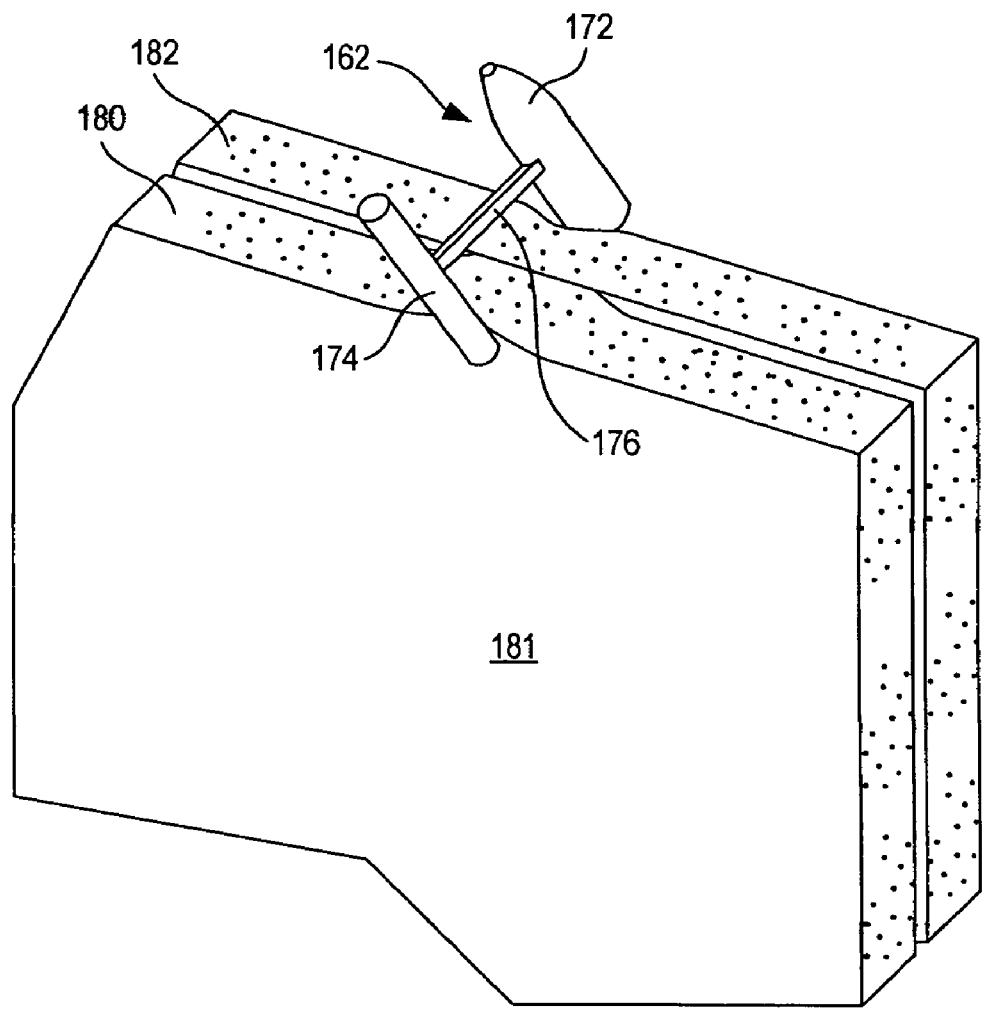
FIG. 9 is a perspective view showing the fastener of the assembly of FIG. 5 fully deployed and securely fastening a pair of tissue layers together.

FIG. 9 illustrates the fastener 162 in its deployed position. It will be noted that the tissue layers 180 and 182 are fastened together between the first member 172 of the fastener 162 and the second member 174 of the fastener 162. The connecting member 176 extends through the tissue layers 180 and 182.

Figure 10:
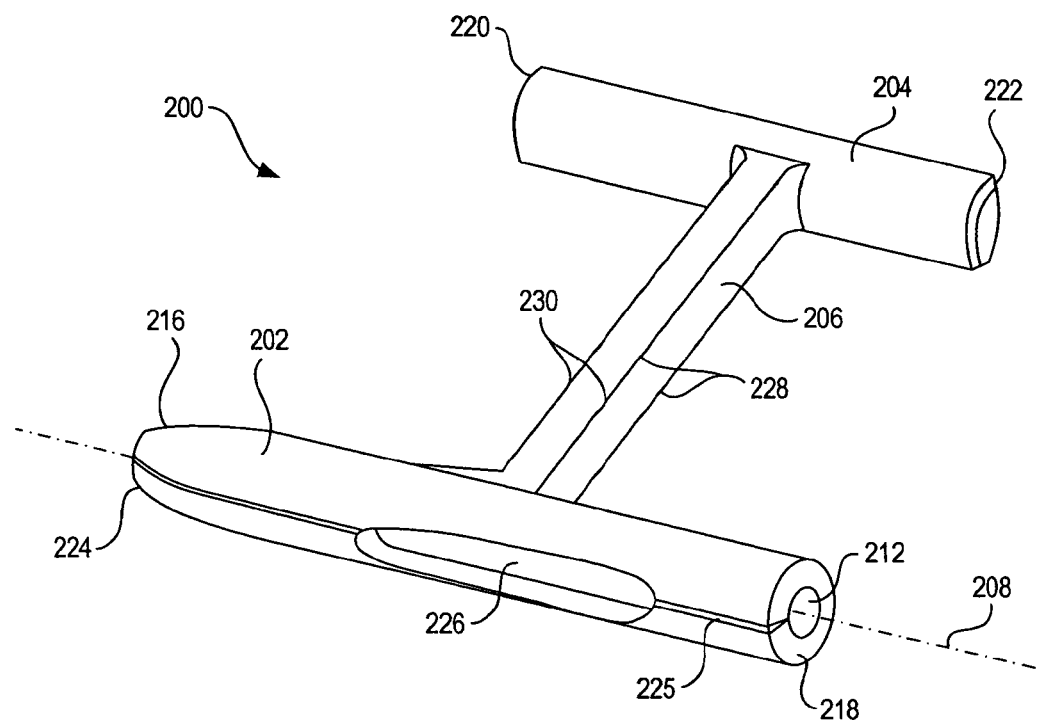
FIG. 10 is a perspective view of a further fastener embodying the invention.
Figure 11:
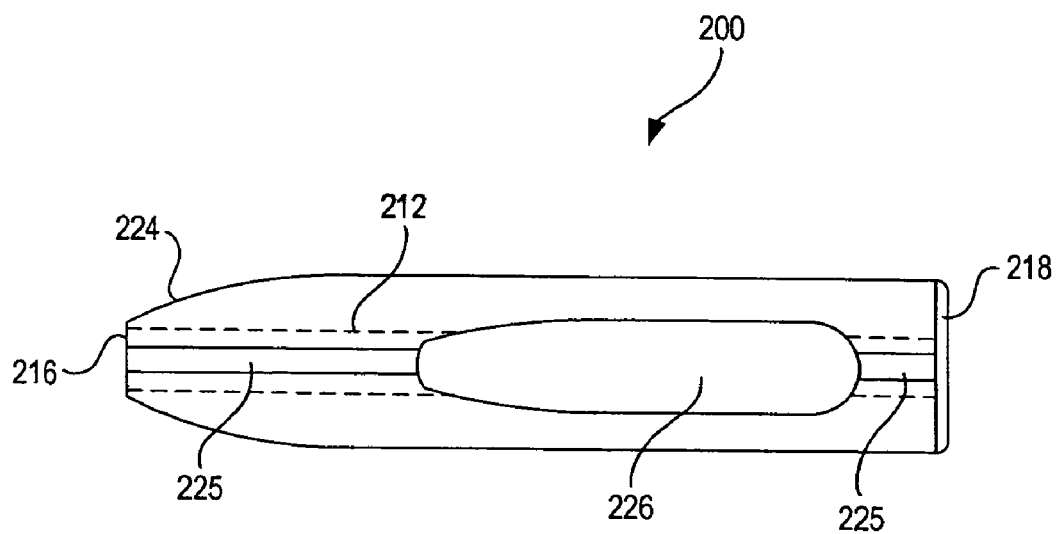
FIG. 11 is a side view of the fastener of FIG. 10.

FIG. 10 is a perspective view and FIG. 11 is a side view of another fastener 200 embodying the present invention. The fastener 200 generally includes a first member 202, a second member 204, and a connecting member 206. As may be noted in FIG. 10, the first member 202 and second member 204 are substantially parallel to each other and substantially perpendicular to the connecting member 206 which connects the first member 202 to the second member 204.

The first member 202 is generally cylindrical or can have any other shape. It has a longitudinal axis 208 and a through channel 212 along the longitudinal axis 208. The through channel 212 is formed by a through bore which is dimensioned to be slidingly received on a tissue piercing deployment wire to be described.

The first member 202 also includes a first end 216 and a second end 218. Similarly, the second member 204 includes a first end 220 and a second end 222. The first end 216 of member 202 forms a pointed dilation tip 224. The dilation tip 224 may be conical and more particularly takes the shape of a truncated cone. The tip can also be shaped to have a cutting edge in order to reduce tissue resistance.

The first and second members 202 and 204 and the connecting member 206 may be formed of different materials and have different textures. These materials may include, for example, plastic materials such as polypropylene, polyethylene, polyglycolic acid, polyurethane, or a thermoplastic elastomer. The plastic materials may include a pigment contrasting with body tissue color to enable better visualization of the fastener during its deployment. Alternatively, the fastener may be formed of a metal, such as stainless steel or a shape memory metal, such as Nitinol.

As may be further noted in FIG. 10, the connecting member 206 has a vertical dimension 228 and a horizontal dimension 230 which is transverse to the vertical dimension. The horizontal dimension is substantially less than the vertical dimension to render the connecting member 206 readily bendable in a horizontal plane. The connecting member is further rendered bendable by the nature of the material from which the fastener 200 is formed. The connecting member may be formed from either an elastic plastic or a permanently deformable plastic. An elastic material would prevent compression necrosis in some applications.

It may be noted in FIGS. 10 and 11, that the first member 202 has a continuous lengthwise slit 225 extending between the first and second ends 216 and 218. The slit 225 includes an optional slot portion 226 that communications with the through channel 212. The slot 226 has a transverse dimension for more readily enabling receipt of a tissue piercing deployment wire during deployment of the fastener 200. Also, because the fastener number 202 is formed of flexible material, the slit 225 may be made larger through separation to allow the deployment wire to be snapped into and released from the through channel 212 as will be seen subsequently. This permits release of the first member 202 during deployment. The slit 225 extends substantially parallel to the through channel 212 and the center axis 208 of the first member 202. It may also be noted that the slit 225 has a width dimension that is smaller or less than the diameter of the through channel 212. This assures that the fastener 200 will remain on a tissue piercing deployment wire as it is pushed towards and into the tissue as will be seen subsequently.

Figure 12:
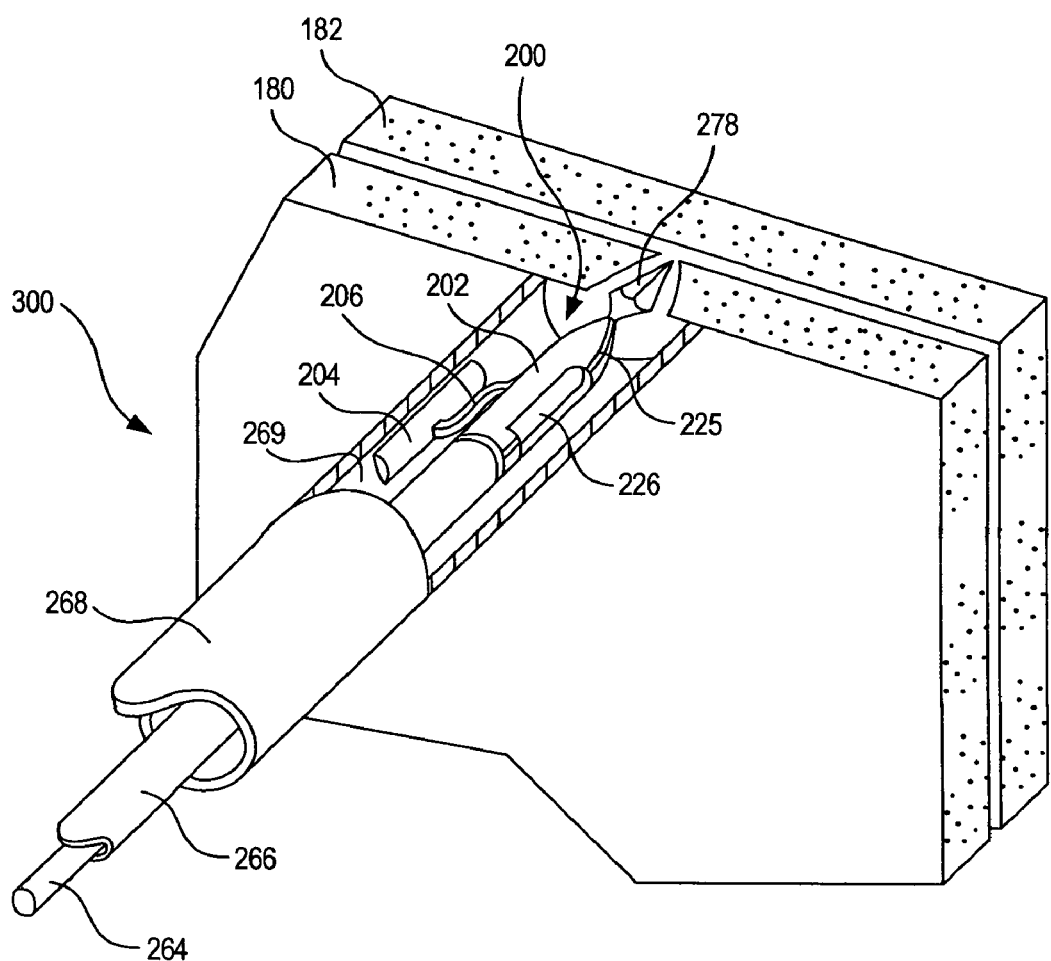
FIG. 12 is a perspective view with portions cut away of a fastener assembly according to another embodiment of the invention with the fastener prepositioned and in an early stage of being deployed.

Referring now to FIG. 12, it is a perspective view with portions cut away of a fastener assembly 300 embodying the present invention for deploying the fastener 200. The tissue layer portions above the fastener 200 have been shown cut away in FIGS. 12-16 to enable the deployment procedure to be seen more clearly. The assembly 300 generally includes the fastener 200, a deployment wire 264, a pusher 266, and a guide tube 268.

The first member 202 of the fastener 200 is slidingly received on the deployment wire 264. The deployment wire 264 has a pointed tip 278 for piercing the tissue layers 180 and 182 to be fastened together and to cut sufficient tissue to enable the fastener member 202 to readily pass through the tissue layers 180 and 182. It may also serve as a guide to guide the wire 264 off of the member 202 at the end of the deployment. The tissue piercing wire 264, fastener 200, and the pusher 266 are all within the guide tube 268. The guide tube 268 may take the form of a catheter, for example, as previously mentioned, or a guide channel within a block of material.

As will be further noted in FIG. 12, and according to this embodiment of the invention the second member 204 is disposed along side the first member 202, with the connecting member between the first member 202 and the second member 204. The second member 204 also trails the first member 202 with respect to the tissue layers 180 and 182. This is all rendered possible due to the flexibility of the connecting member 206.

With the first member 202 of the fastener 200 slidingly received on the tissue piercing wire 264 and with the pusher 266 just touching the first member 202 on the tissue piercing wire 264, the tip 278 of the tissue piercing wire 264 pierces the tissue layers 180 and 182. The subassembly of the tissue piercing wire 264, fastener 200, and pusher 266 may be guided to its intended location relative to the tissue layers 280 and 282 by the guide tube 268.

Figure 13:
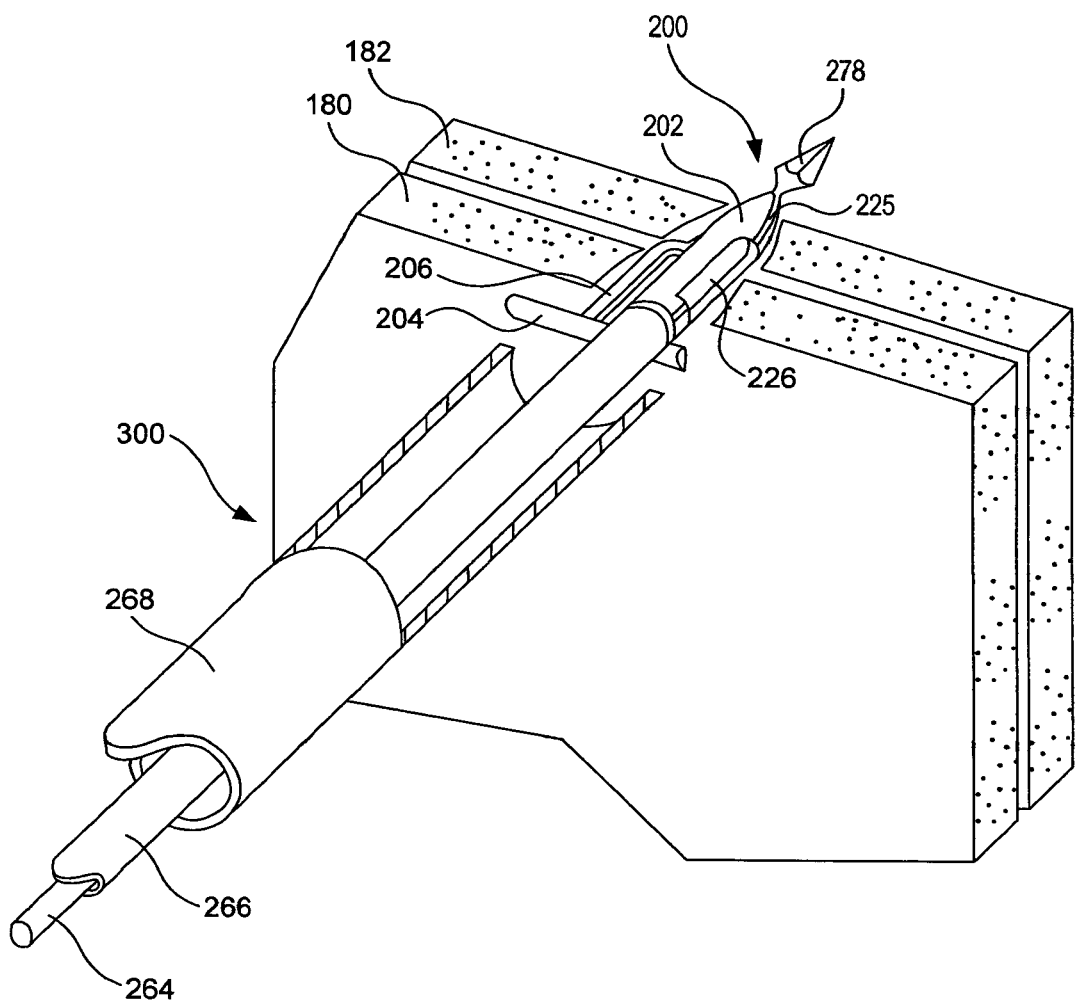
FIG. 13 is a perspective view of the assembly of FIG. 12 shown with the fastener being driven in the tissue layers to be fastened.

As shown in FIG. 13, the tissue piercing wire 264 has pierced the tissue layers 180 and 182 and the pusher 266 has pushed the first member 202 of the fastener 200 through the tissue layers 180 and 182 on the tissue piercing wire 264. This may be accomplished by moving the wire 264 and the pusher 266 together.

Figure 14:
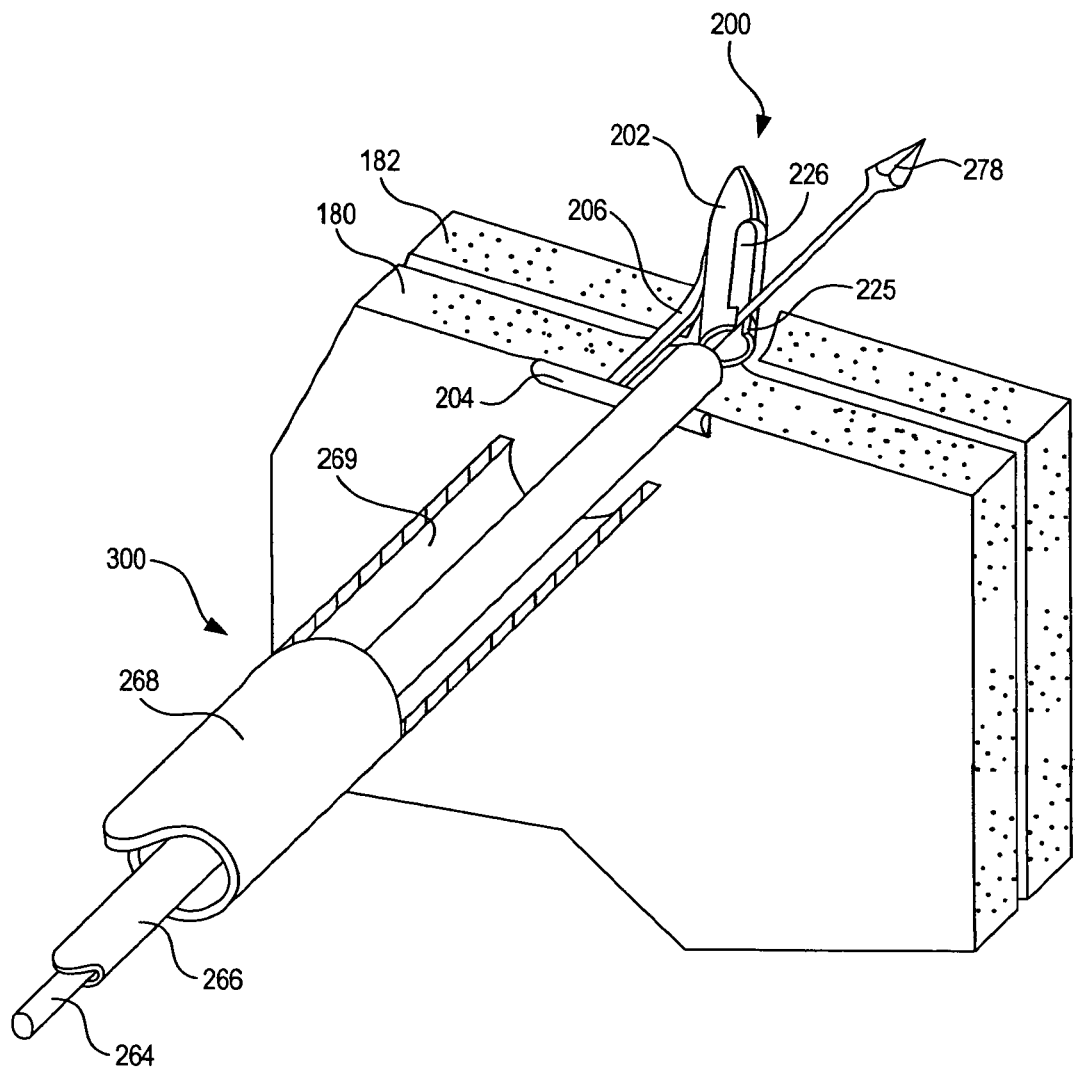
FIG. 14 is a perspective view of the assembly of FIG. 12 shown with the fastener in an intermediate stage of deployment.

As may be seen in FIG. 14, wire 264 has been pushed further forward and independently from the first member 202 and the pusher 266. The first member 202 has also been pushed forward by the pusher 266 to cause the second member 204 to engage the tissue layer 180. Continued pushing of the first member 202 causes the first member to pivot in a counter clockwise direction because the second member 204 is held by the tissue layer 180. The counter clockwise movement of the first member 202 causes the wire 264 to spread the slit 225 open, to pass down the slit to enter slot portion 226 and to eventually pass through the slit 225 at end 218. The fastener 200 is then released from the wire 264.

Figure 15:
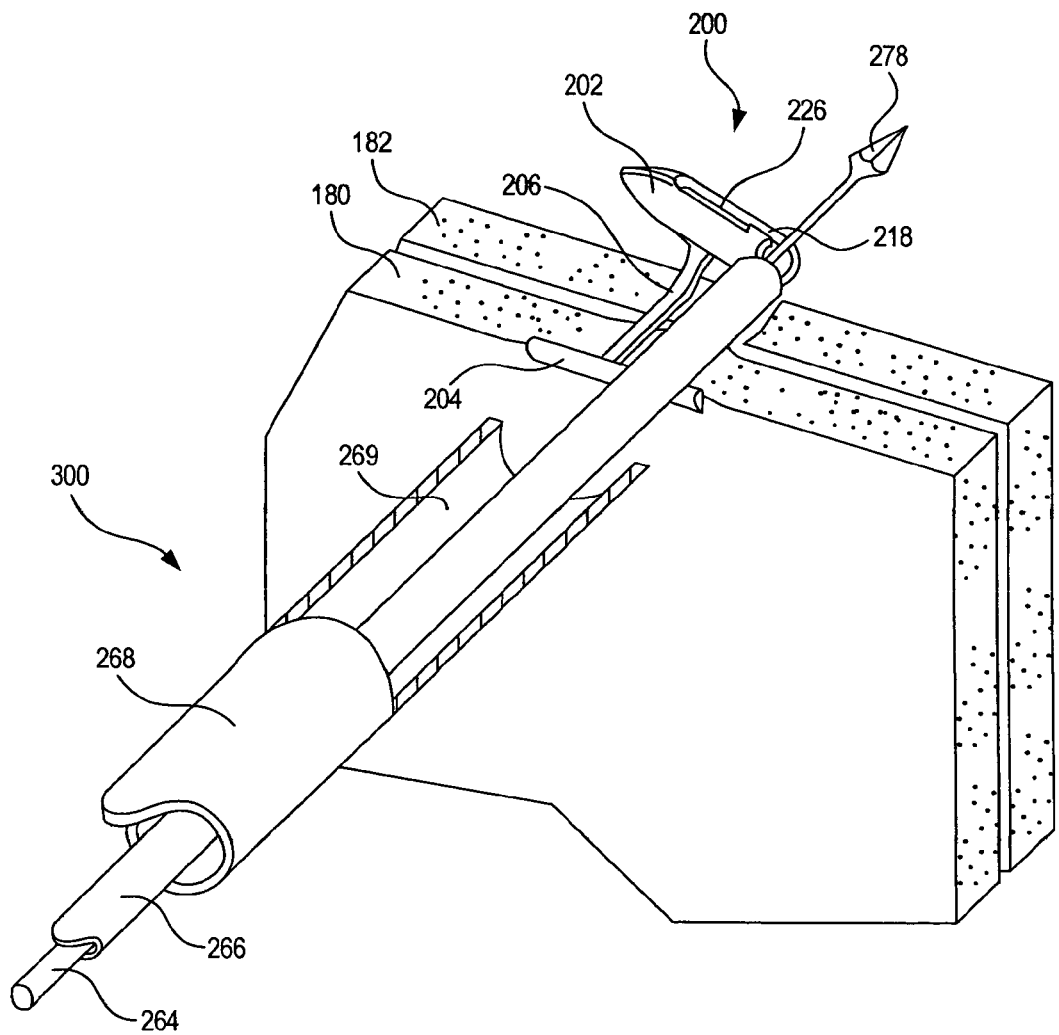
FIG. 15 is a perspective view of the assembly of FIG. 12 shown with the fastener almost completely deployed.

In FIG. 15, it will now be seen that the second end 218 of the first member 202 has cleared the wire 264 and tissue layer 182. The tissue piercing wire 264 may now be retracted into the pusher 266 and the tissue piercing wire 264 and pusher 266 may be withdrawn.

Figure 16:
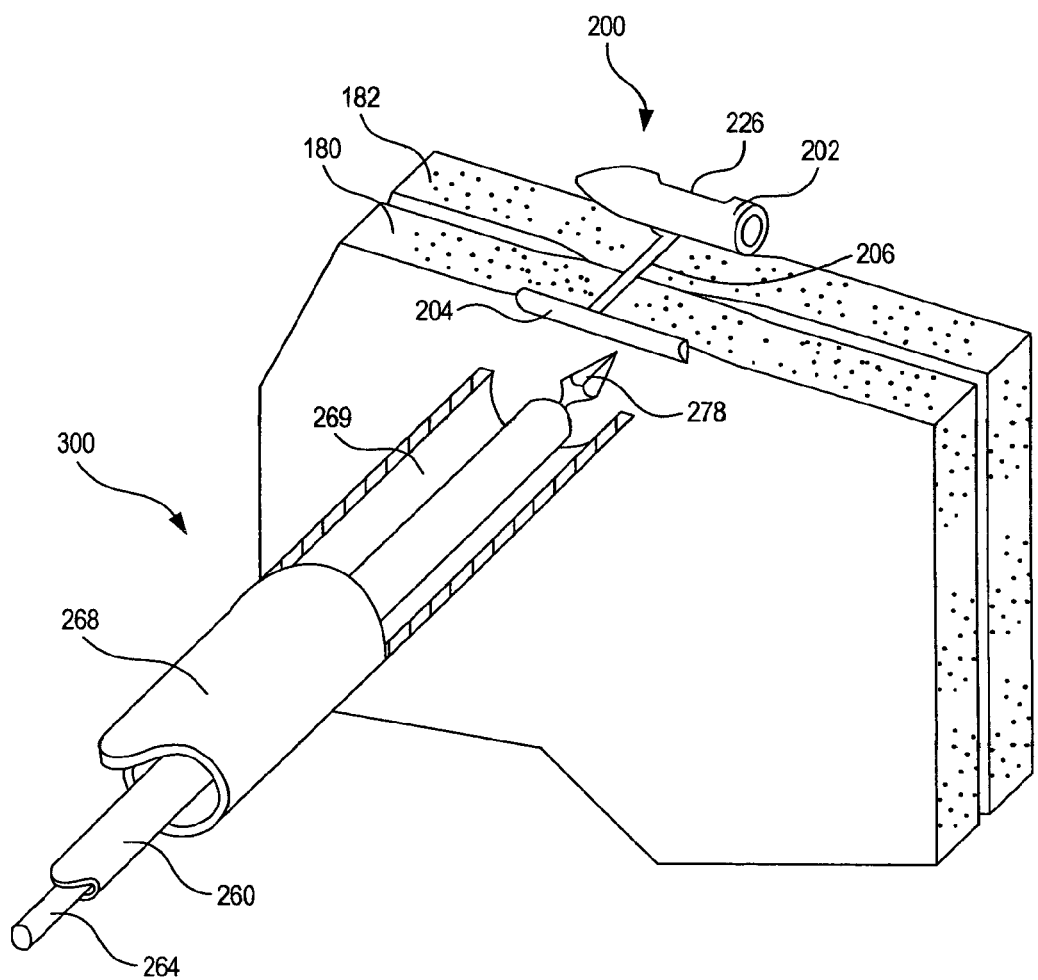
FIG. 16 is a perspective view showing the fastener of the assembly of FIG. 5 fully deployed.

FIG. 16 illustrates the fastener 200 in its fully deployed position. It will be noted that the fastener has returned to its original shape. The tissue layers 180 and 182 are fastened together between the first member 202 of the fastener 200 and the second member 204 of the fastener 200. The connecting member 106 extends through the tissue layers 180 and 182.

Figure 17:
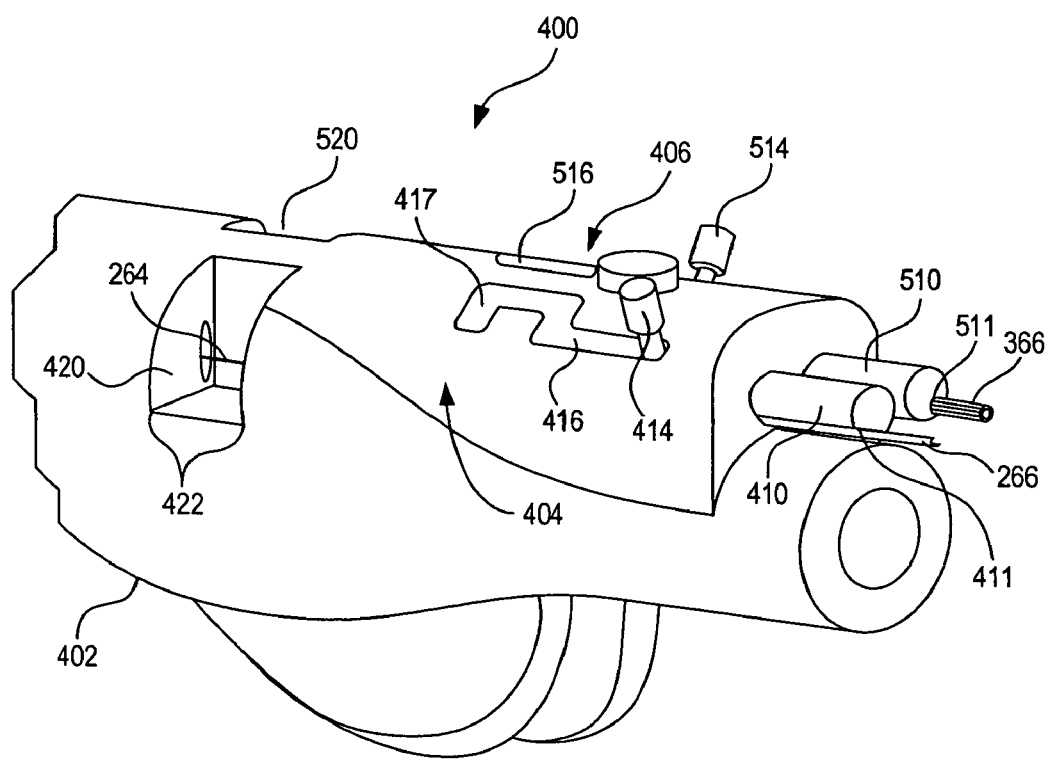
FIG. 17 is a perspective view of a fastener assembly according to an embodiment of the invention.
Figure 18:
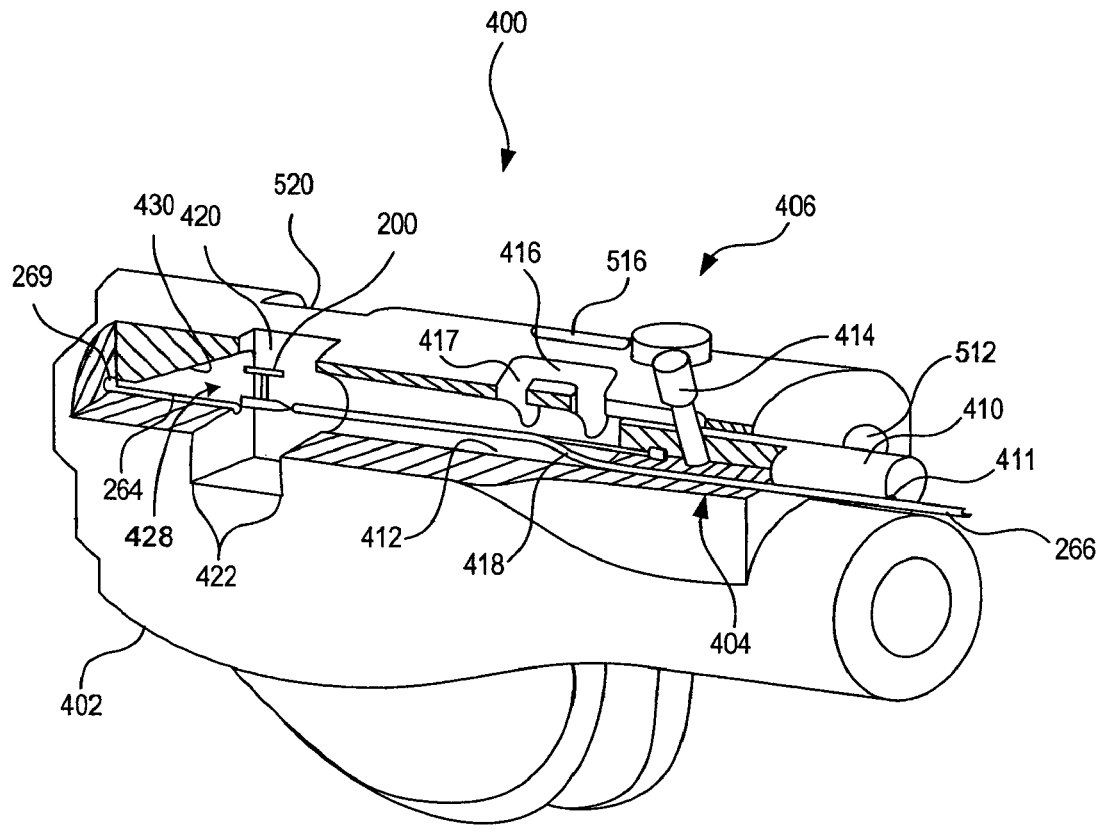
FIG. 18 is a perspective view, with portions cut away, of the assembly of FIG. 18 showing a fastener being driven into a fastener configuration structure according to an embodiment of the invention.

Referring now to FIGS. 17 and 18, FIGS. 17 and 18 illustrate a control assembly 400 for controlling the delivery and deployment of fasteners according to an embodiment of the present invention. More specifically, the assembly 400, according to this embodiment, is adapted to be located at the proximal end of an assembly, such as those shown in FIGS. 5-9 and 12-16 for deploying fasteners into stomach tissue for maintaining manipulated stomach tissue which has been folded and molded to restore a GEFV flap.

The assembly 400 generally includes a housing 402. The housing includes identical, side-by-side control assemblies 404 and 406. Since the control assemblies 404 and 406 are identical, only assembly 404 will be described in detail herein.

The assembly 404 includes a bolt 410, a receiver 412 that slidingly receives the bolt 410 and the pusher 266. Projecting from the bolt is a handle 414. The handle extends through a track 416 in the housing 402 and restricts and measures the movement of the bolt 410.

As previously mentioned, the control assemblies 404 and 406 are side-bi-side and identical. Hence, the assembly 406 may also be seen to include a bolt 510, a pusher 366, a receiver 512, and a handle 514 projecting through a track 516. The operation of the assembly 406 is identical to the operation of the assembly 404 to be described subsequently.

The assembly 404 still further includes a fastener loading station 420. The loading station 420 has a length dimension 422 sufficient to receive a fastener loader to be described subsequently with respect to FIG. 20. The fastener loader and loading station facilitate loading of fasteners onto the deployment stylet 264. The assembly 406 also includes such a loading station 520.

As may be best seen in FIG. 18, the bolt 410 of assembly 404 is attached to the proximal end of the stylet 264. Hence, the bolt and stylet are arranged for linear movement when the bolt 410 is moved within the receiver 412 with the handle 414 along the track 416.

The pusher 264 intersects the path of the stylet 264 at an intersection point 418. The pusher, as best described in copending application Ser. No. 11/043,903, includes an opening at the intersection 418. The opening permits the stylet to be fed into the pusher and hence to allow the pusher 266 to be carried by the stylet 264 distal to the intersection 418. As previously seen, this permits the pusher 266 to engage the fastener 200. Also, the loading station 420 is distal to the intersection 418 to permit the fastener 200 to be loaded onto the stylet 264 and engaged by the pusher 266.

The bolt 410 further includes a lumen 411 that slidingly receives the pusher 266. This permits the movement of the pusher 266 to be controlled independently of the movement of the bolt 410 and the stylet 264. The bolt 510 also includes such a lumen 511 as may be seen in FIG. 17.

As may be further noted in FIG. 18, the assembly 404 further includes a fastener configuration structure 428 including a funnel shaped wall 430 between the loading station 420 and the guide lumen 269. As may be recalled from FIGS. 12-16, the guide lumen 269 guides the stylet 264, fastener 200, and pusher 266 to the desired location for deploying the fasteners. The funnel shaped wall 430 serves to preposition the second member 204 of the fastener 200 within the guide lumen 269 as best seen in FIG. 12. The second member 204 is prepositioned as a trailing member along side the first member 202 with the connecting member 206 therebetween. This fastener configuration and prepositioning assists in the proper functioning of the second member 204 as the fastener 200 is deployed. The second member 204 is automatically rendered in its preposition along side the first member 202 with the connecting member 206 therebetween as the fastener 200 is translated distally through the funnel shaped wall section towards the guide lumen 269.

Figure 19:
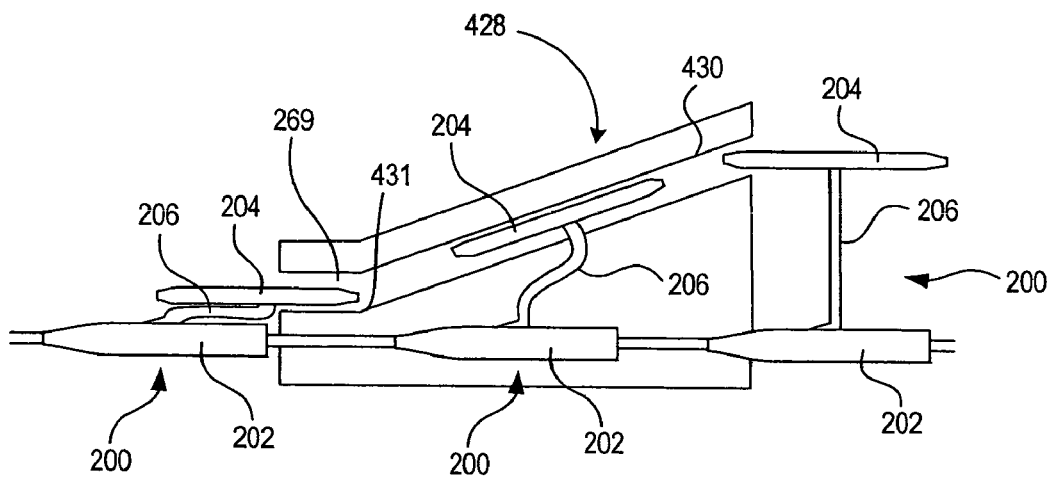
FIG. 19 is a simplified side view, partly in section, of the fastener configuration structure of FIG. 19.

FIG. 19 illustrates this in greater detail. Here we see a fastener 200 as it is pushed through the fastener configuration structure 432. As the fastener enters the fastener configuration structure 428, the second member 204 of the fastener 200 engages the funnel shaped wall 430. The funnel shaped wall 430 guides the second member 204. As the second member 204 follows the funnel shaped wall downward, it begins to trail the first member 202. Also, the connecting member 206 is folded back to be between the first member 202 and the second member 206 of the fastener 200. As a result, by the time the fastener 200 reaches the fastener configuration outlet 431 communicating with the guide lumen 269, the second member 204 is automatically disposed trailing and along side the first member 202 with the connecting member 206 therebetween. The fastener is now configured for dependable deployment.

When it is time to advance the stylet 264 in through the tissue as shown in FIG. 15, for example, the handle 414 of assembly 400 is moved in a distal direction forcing the stylet 264 to move distally. The handle and thus the stylet movement is restricted and measured by a transverse portion of slot 417 of the track 416. The handle 414 may be locked in a longitudinal position within the transverse portion 417 of the track. The fastener 200 is advanced by the pusher 266. After a fastener is deployed, the distal end of the pusher is drawn back to be proximal to the loading station 420 to permit another fastener to be loaded onto the stylet 264.

The fasteners are loaded onto the stylet by presenting the slit 225 of the fasteners to the stylet. The slit 225 (FIG. 11) is widened by the stylet 264 and the stylet 264 slips through the slit 225 and into the through channel 212 of the fastener first member 202.

Figure 20:
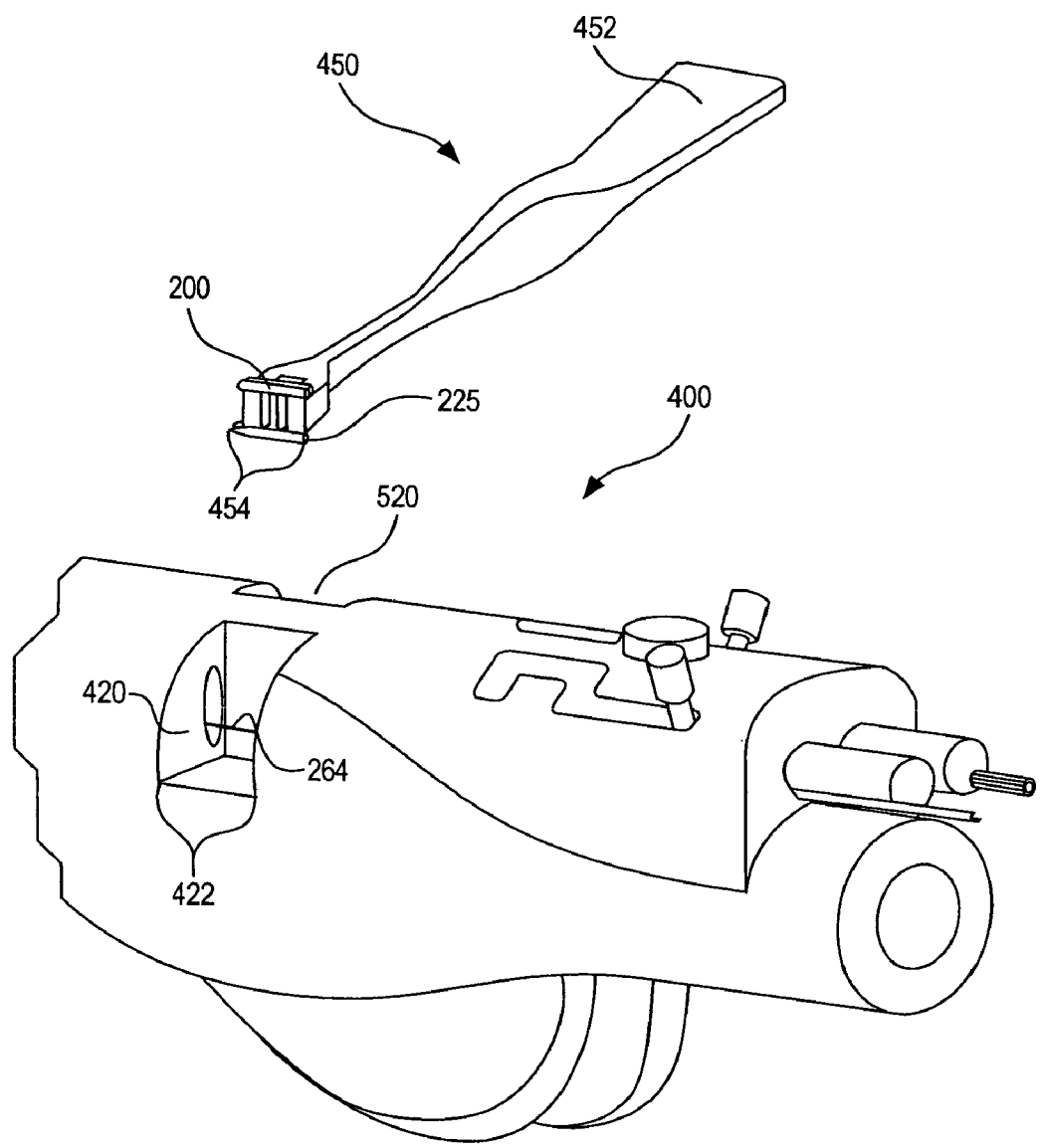
FIG. 20 is a perspective view of the assembly of FIGS. 18 and 19 along with a fastener loader according to an embodiment of the invention for loading fasteners into the deployment assembly.

FIG. 20 shows a fastener loader 450 which may be employed for loading the fasteners onto the stylet. The loader 450 has a handle 452 permitting it to be readily hand-holdable. At the distal end, the loader is arranged to carry a plurality of fasteners 200. The loader presents the fasteners so that the slit 225 will be aligned with the stylet 264.

The holder has a width dimension 454 that is less than the length dimension 422 (FIGS. 17 and 18) of the loading station 420. Hence, as seen in FIG. 20, the loader 450 may be inserted into a loading station for mounting a fastener onto a corresponding stylet. The loader 450 may be used on either side of the assembly 400 for loading a fastener onto stylet 264 at loading station 420 or loading a fastener onto stylet 364 at loading station 520.

While particular embodiments of the present invention have been shown and described, modifications may be made, and it is therefore intended in the appended claims to cover all such changes and modifications which fall within the true spirit and scope of the invention.

What is claimed is:

1. A method comprising:
  providing a fastener including a first member, a second member, the first and second members having first and second ends, and a flexible connecting member fixed to each of the first and second members intermediate the first and second ends and extending between the first and second members, the first member having a longitudinal axis and a through channel along the axis, the first member of the fastener has a lengthwise slit communicating with the through channel;

mounting the fastener onto a deployment wire with the deployment wire slidingly received by the through channel of the first member, the deployment wire being moved into the through channel by introducing the deployment wire through the lengthwise slit, the mounting step includes causing the deployment wire to be received within the through channel through the slit;

translating the fastener to within a lumen dimensioned to receive the fastener and deployment wire and which guides the deployment wire and fastener to tissue; and orientating the second member in a predetermined position relative to the first member as the fastener is translated to within the lumen, the second member being oriented by passing the second member of the fastener adjacent a funnel-shaped wall which moves the second member to a position which is closer to the first member, the funnel-shaped wall also causing the second member to trail the first member as the fastener is translated through the lumen to the tissue.

2. The method of claim 1, wherein the orientating step comprises positioning the second member along side the first member.

3. The method of claim 1, wherein the orientating step comprises orientating the second member along side the first member with the connecting member between the first and second members.

4. The method of claim 1, wherein the orientating step comprises orientating the second member along side the first member with the connecting member between the first and second members and with the second member trailing the first member.

* * * * *